United States Patent [19]

Ellingboe

[11] Patent Number: 5,656,027
[45] Date of Patent: Aug. 12, 1997

[54] SURGICAL FLUID SUCTION ACCUMULATOR AND VOLUME MEASUREMENT DEVICE

[75] Inventor: Bruce S. Ellingboe, Littleton, Colo.

[73] Assignee: Cobe Laboratories, Inc., Lakewood, Colo.

[21] Appl. No.: 472,990

[22] Filed: Jun. 6, 1995

[51] Int. Cl.⁶ ............................. A61M 31/00; A61M 1/00
[52] U.S. Cl. .......................... 604/49; 604/65; 604/67; 604/118; 604/119; 604/318; 604/320; 604/902; 137/205
[58] Field of Search .................................. 604/4, 49, 50, 604/65, 66, 67, 118, 119, 318, 319, 320, 902; 137/205

[56] References Cited

U.S. PATENT DOCUMENTS

| | | | |
|---|---|---|---|
| 3,866,608 | 2/1975 | Reynolds et al. | 604/319 X |
| 3,918,453 | 11/1975 | Leonard | 604/67 |
| 4,781,707 | 11/1988 | Boehringer et al. | 604/319 X |
| 5,055,198 | 10/1991 | Shettigar | 604/319 X |
| 5,378,227 | 1/1995 | O'Riordan | 604/4 |
| 5,407,425 | 4/1995 | Werner et al. | 604/4 |

Primary Examiner—Mary Beth Jones
Attorney, Agent, or Firm—Bruce R. Winsor; Edna M. O'Connor

[57] ABSTRACT

An apparatus for minimizing trauma to a medical fluid while transporting the medical fluid from a surgical wound by reducing the air to fluid interface during transport. The apparatus includes a suction wand for collecting medical fluid and tubing for transporting the medical fluid to a reservoir. The reservoir repeatedly accumulates the medical fluid and discharges it in a bolus when a predetermined volume is achieved. The reservoir comprises a fluid inlet, a fluid outlet, and a gas outlet. A siphon is disposed inside the reservoir for removing the bolus of medical fluid once the predetermined fluid volume is accumulated. The siphon includes a first end for suctioning the medical fluid and a second end exiting the reservoir through the fluid outlet, thereby defining an external siphon length. A pump is attached to the second siphon end to provide suction to the system. A bypass line connects the reservoir, from its gas outlet, to the external siphon length thereby removing air from the reservoir and, thus, increasing the reduction of the air to fluid interface during transport of the medical fluid.

17 Claims, 3 Drawing Sheets

SURGICAL FLUID SUCTION ACCUMULATOR AND VOLUME MEASUREMENT DEVICE

FIELD OF INVENTION

The present invention relates to collecting and measuring surgical fluid during the course of a surgical procedure. More particularly, the present invention relates to minimizing trauma to blood, recovered and measured during surgery, so that it may be harvested for later use or returned to the patient.

BACKGROUND OF THE INVENTION

During a surgical procedure it is often desirable to recover blood from the surgical wound and return it to the patient or harvest it for later use in blood salvaging procedures. Blood is typically recovered by suctioning it from the surgical wound, using a suction wand, through a tubing set into a collection reservoir. Suction wands generally aspirate both air and blood causing a turbulent flow in the suction wand and numerous blood to air interfaces as the blood is transported through the tubing set to the collection reservoir, blood oxygenator, blood salvaging device or the like. This turbulent flow in the suction wand coupled with blood transport having many blood to air interfaces, has been found to be a major source of blood trauma, particularly during open heart surgery. Furthermore, blood exposed to air may coagulate and form clots, thus, becoming unsuitable for reinfusion to the patient or for later use in blood salvaging procedures.

In the conventional system, this blood flow having many blood to air interfaces, must travel through a long tubing length before being collected in a collection reservoir, or processed by a blood oxygenator, blood salvage device or the like. Furthermore, in the conventional system the amount of suction applied to the suction wand typically remains constant throughout a surgical procedure. This constant suction does not account for the erratic and variable flow rate of patient blood losses during a surgical procedure; therefore, the same amount of suction is applied during low flow rates of patient blood losses as during high flow rates. Using a high amount of vacuum to suction blood during low flow rates may increase the amount of air aspirated into the tubing set along with patient blood. This may not only increase the turbulent blood flow, but may also increase the air to blood interface, thereby increasing the potential for blood trauma.

It is, therefore, desirable to reduce the turbulence of blood flow in blood salvaging procedures. It is also desirable to reduce the distance that salvaged blood must travel in contact with air. Further, it is desirable to reduce the air to blood interface in blood salvaging procedures.

SUMMARY OF THE INVENTION

A significant aspect of the present invention is a device and method for reducing the surface area of blood to air interfaces in the blood collection lines used in blood salvaging during surgical procedures.

Another significant aspect of the present invention is a method and device for reducing the distance that salvaged blood must travel while containing a significant quantity of air to blood interfaces.

Another significant aspect of the present invention is a method and device for reducing the amount of air to blood interfaces in blood collection lines during blood salvaging.

Another significant aspect of the present invention is method and device for measuring a rate of blood flow from a patient's surgical wound to the blood receiving reservoir.

Another significant aspect of the present invention is a method and device for warning a medical care worker of excessive patient bleeding.

Another significant aspect of the present invention is a method and device for measuring the volume of blood salvaged during a surgical procedure.

Another aspect of the present invention is a device and method for reducing the turbulence of blood flow by reducing the amount of air aspirated with the blood from the surgical wound by controlling the amount of suction or vacuum applied to the system.

In accordance with the above aspects the present invention provides a blood accumulator having a fluid collector connected to a reservoir by a tubing collector line. A siphon is disposed inside the reservoir. The siphon has a tubing end that extends below the reservoir's exterior and communicates with a vacuum source. An air bypass line connects the upper interior of the reservoir with external siphon tubing.

The vacuum source creates suction or a vacuum in the reservoir and, therefore, in the fluid collector and tubing connector line. Blood and air are suctioned through the fluid collector and tubing connector into the reservoir. The blood accumulated in the bottom of the reservoir while air is drawn out of the reservoir by the bypass line. When the blood level reaches the top of the siphon, the blood is siphoned out of the reservoir as a single bolus having a continuous flow. The air to blood interfaces of prior art blood collectors are reduced because air is separated from the received patient blood and the blood is transported in large boluses.

When the blood level reaches the top of the siphon, a fluid level sensor may be activated. The fluid level sensor reports each activation to a controller. The volume of blood contained in the reservoir when the fluid level sensor is activated is predetermined by the configuration of the reservoir. The controller may count the sensor activations over the course of a procedure and during given time periods to determine the total volume of blood processed and the rate at which blood is flowing from the patient to the reservoir. The controller may adjust the amount of vacuum or suction applied to the system, when the rate of patient blood flow to the reservoir decreases, thereby reducing the amount of air aspirated with blood by the fluid collector and, thus, reducing turbulent flow in the suction wand.

The controller may be programmed to activate an alarm when the rate of patient blood flow to the reservoir exceeds a predetermined threshold. Similarly, the controller may be programmed to activate an alarm when no blood flow is detected over a predetermined time period indicating that the suction wand is not positioned correctly.

Other objects of this invention will appear from the following description and appended claims, reference being had to the accompanying drawings forming a part of this specification wherein like reference characters designate corresponding parts in the several views.

DETAILED DESCRIPTION OF THE PREFERRED EMBODIMENT

Figure 1:
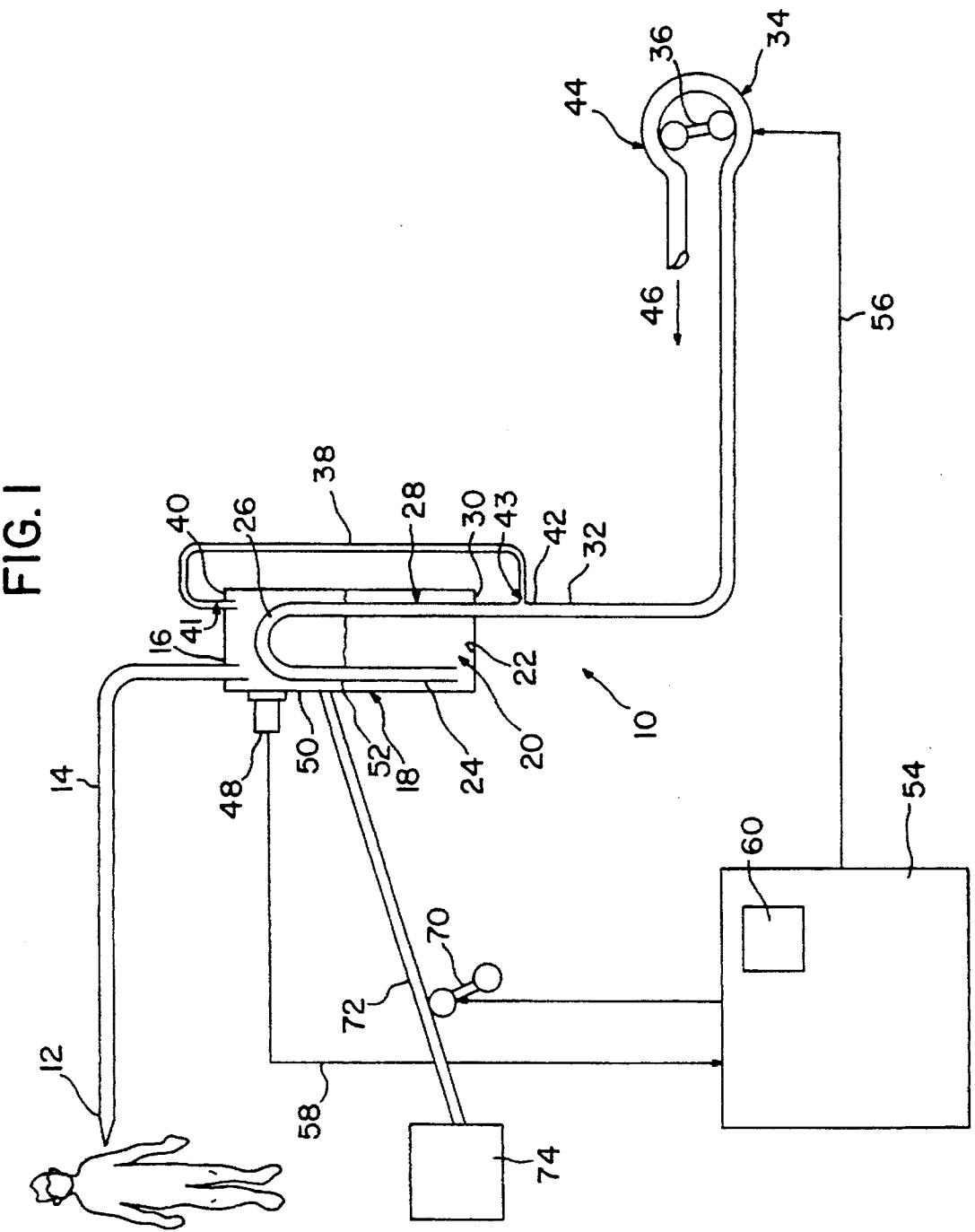
FIG. 1 is a schematic diagram of the blood accumulator of the present invention in communication with a controller and pump.

FIG. 1 schematically illustrates the blood accumulator 10 of the present invention. The blood accumulator comprises a fluid collector 12 for collecting or receiving blood or other biological fluids from a patient during a surgical procedure. The fluid collector 12 may comprise any one of the well known devices used for salvaging blood from a patient during surgery, including a suction wand. The fluid collector 12 is connected to a tubing connector 14 that transports the received blood to the fluid inlet 16 of the blood receiving reservoir 18. The tubing connector 14 may comprise a piece of tubing having a length of about twelve to eighteen inches. It is preferred that the tubing connector 14 comprise the shortest length that is practical for the blood salvage system design, thereby minimizing the distance blood must travel while having a large surface area of blood to air interfaces. Alternatively, the blood accumulator 10 may be incorporated directly into the suction wand, to minimize the distance that blood is transported having numerous blood to air interfaces as will be discussed in more detail in FIG. 5.

A siphon 20 is disposed in the interior 22 of the blood receiving reservoir 18. The siphon 20 comprises a first tubing length 24, a top 26, and a second tubing length 28. The second tubing length 28 extends through the reservoir outlet 30 to the exterior of the reservoir thereby forming an exterior siphon length 32 which is disposed below the first siphon tubing length 24. It is important that the exterior tubing length 32 be disposed below the first siphon tubing length 24 for the siphon 20 to function, as will be discussed in more detail below. An end 34 of the exterior tubing length 32 is engaged by a vacuum source 36. The vacuum source may comprise a peristaltic pump (FIG. 1), a vacuum pump (FIG. 2), or any one of the other types of medical pumps well known by those skilled in the art.

An air bypass line 38 connects an upper portion of the reservoir interior 22 with the exterior tubing length 32. A first end 41 of the air bypass line 38 connects to the blood receiving reservoir 18 at the reservoir's air outlet 40. A second end 43 of the air bypass line 38 connects to the exterior tubing length 32 at a junction 42. It will be apparent to those skilled in the art that the air bypass line 38 may be disposed inside the reservoir having an end disposed above the top 26 of the siphon 20 and an opposing end connecting to the second tubing length 28.

Where the vacuum source 36 is a peristaltic pump, it creates a vacuum in the exterior tubing length 32 which in turn creates a vacuum in the reservoir 18. The vacuum in the reservoir 18 creates a vacuum in the fluid collector 12 and the tubing connector line 14, thereby suctioning blood and other fluids from the surgical wound to the reservoir 18. The vacuum source 36 may draw the blood or biological fluid through a tubing set 44, as denoted by the direction arrow 46, to a storage reservoir (not shown). For example, in a cardiac bypass operation, the vacuum source 36 may draw fluid to a blood oxygenator reservoir (not shown) or to a cardiotomy reservoir (not shown).

Figure 2:
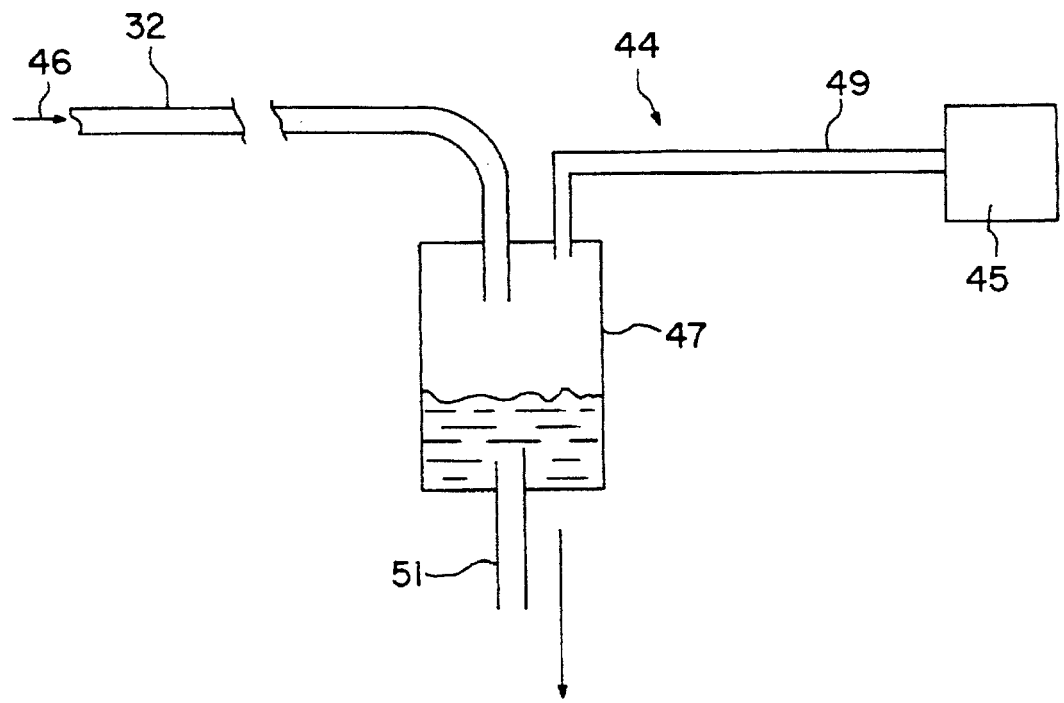
FIG. 2 is a schematic diagram showing the configuration of the external siphon tubing length of the present invention when the vacuum source is a vacuum pump.

In blood salvage operations, the vacuum source 36 may be a vacuum pump 45 as shown in FIG. 2. The vacuum pump 45 is connected to a storage reservoir 47 by a tubing line 49. The vacuum pump 45 creates a vacuum in the storage reservoir, creating a vacuum in the external tubing length, in turn creating a vacuum in the blood receiving reservoir 18 which creates a vacuum in the fluid collector 12 for suctioning fluid from the surgical wound. The suctioned fluid is drawn by the vacuum pump 45 to the storage reservoir 47 where a peristaltic pump (not shown) may draw the blood through line 51 to a blood processor (not shown).

Referring again to FIG. 1, a fluid level sensor 48 is affixed to an upper portion of the reservoir wall 50. The fluid level sensor 48 may extend through the reservoir wall 50 to the reservoir interior 22. The fluid level sensor 48 may not extend through the reservoir wall 50 where it is of a type that functions from outside the reservoir, such as an ultrasonic or optical sensor. The fluid level sensor 48 is positioned to detect a fluid level 52 of blood or biological fluid in the siphon 20 when the fluid level 52 reaches the top 26 of the siphon 20. The fluid level sensor 48 may be an optical sensor, capacitive sensor, ultrasonic sensor or any one of the many non-invasive fluid level sensors well known in the art. The volume of fluid the reservoir 18 contains when the fluid level 52 reaches the top 26 of the siphon 20 must be sufficiently large such that when the accumulated fluid is transported through the tubing 32 the surface area of air to blood interfaces is significantly reduced. It is preferred that the reservoir contain at least 5 milliliters when the fluid level 52 reaches the top 26 of the siphon 20.

A controller 54 communicates with the fluid level sensor 48 and the vacuum source 36 through conventional electrical interconnects 56, 58. The controller may comprise one or more micro processors. The controller 54 may further comprise an alarm 60.

Figure 3:
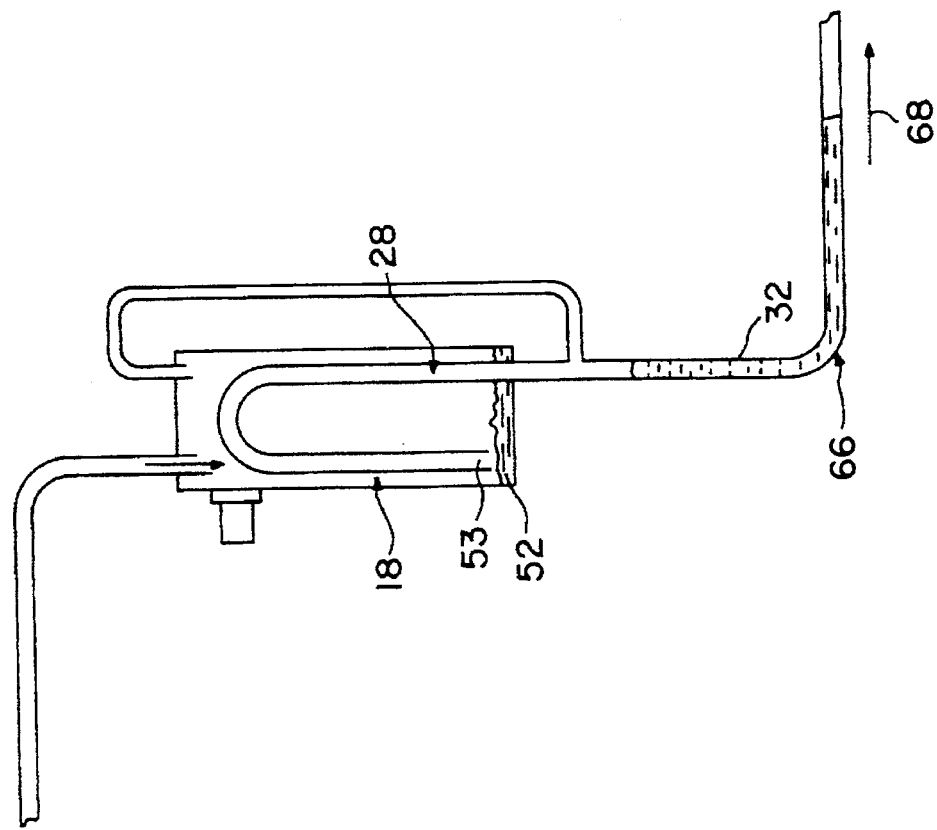
FIG. 3 is a schematic diagram of the blood accumulator having the fluid level at its predetermined maximum.
Figure 4:
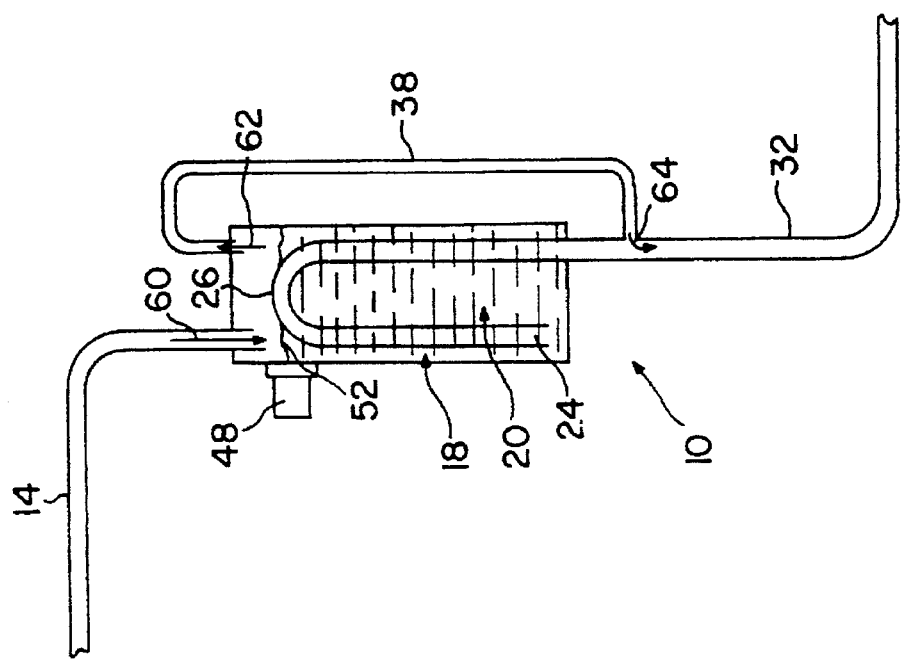
FIG. 4 is a schematic diagram of the blood accumulator where the fluid has been siphoned out of the reservoir and is being transported in a bolus towards the source of vacuum.

FIGS. 3 and 4 schematically illustrate the accumulator 10 when the fluid level 52 reaches the top 26 of the siphon 20 and shortly thereafter. As discussed above, when suction or a vacuum is applied to the external tubing length 32, mixed blood and air are in turn drawn through the fluid collector 12 (FIG. 1), through the tubing connector line 14 and into the reservoir 18 as denoted by the direction arrow 60. The blood and air separate in the reservoir 18, the blood accumulates in the bottom of the reservoir 18 while the air is removed from the reservoir 18 by the air bypass line 38 as denoted by the direction arrow 62. The air bypass line 38 draws the air into the external tubing length 32, as denoted by the direction arrow 64, during the time in which the blood accumulates in the reservoir 18.

Hydrostatic pressure forces the blood up the first siphon tubing length 24. When the blood level 52 reaches the top 26 of the siphon 20, thereby priming the siphon, the weight of the fluid bolus 66 causes the blood to travel down the second siphon tubing length 28 into the external tubing length 32 towards the vacuum source 36, as denoted by the direction arrow 68, in a continuous flow. Because the reservoir 18 empties rapidly when the fluid level 52 reaches the top 26 of the siphon, air is pulled into the reservoir 18 rather than through the bypass line 38 into the external tubing length 32 during this time. Thus, the surface area of air to blood interfaces are reduced by the present invention.

Once the fluid has exited the reservoir 18 in a bolus, the fluid level 52 of the fluid remaining in the reservoir is below the tip 53 of the first siphon tubing length unless patient blood flow is very rapid. The blood continues to accumulate in and exit the reservoir 18, in the above described siphon cycles, as long as suction or a vacuum is applied to the system. Where blood flow from the surgical wound to the reservoir 18 is sufficiently rapid, blood will be removed from the reservoir 18 continuously rather than accumulating and evacuating through the above described siphon cycle.

Referring to FIGS. 1 through 3, the fluid level sensor 48 is activated every time the fluid level 52 reaches the top 26 of the siphon 20. The fluid level sensor 48 signals the controller 54 each time that it is activated. The controller 54 may measure the time $t_f$ it takes for the reservoir 18 to refill with fluid which is determined by measuring time between the release of the previous fluid level sensor 48 activation and a new activation. Because the fluid level sensor 48 is positioned to detect fluid in the top 26 of the siphon 20, and the siphon 20 remains full until the reservoir fluid level 52 drops below the siphon tip 53, the controller 54 may measure the time $t_e$ it takes for the reservoir 18 to empty by measuring the time between a fluid level sensor 48 activation and release of the activation. The reservoir 18 contains a predetermined volume $V_a$ of blood when the blood fluid level 52 reaches the top 26 of the siphon 20 and activates the fluid level sensor 48.

The controller 54 may calculate the total blood volume salvaged $V_t$ during a given procedure as follows:

$$V_t = Q_b(T_f + t_e)$$

where $Q_b$ = rate at which blood is flowing from the patient to the reservoir 18.

The controller 54 may divide the predetermined reservoir volume $V_a$ by the time $t_f$ it takes the reservoir 18 to fill or refill to determine the rate $Q_b$ at which blood is flowing from the patient to the reservoir 18. If the controller 54 detects a change in rate at which blood is flowing into the reservoir 18, the controller 54 may instruct the vacuum source 36 to adjust the amount of vacuum or suction it is applying to the external tubing length 32. If the rate at which blood is flowing into the reservoir 18 increases, the controller 54 may instruct the vacuum source 36 to increase the amount of suction or vacuum it is applying. Conversely, if the rate at which blood is flowing into the reservoir 18 decreases, the controller 54 may instruct the vacuum source 36 to decrease the amount of suction or vacuum, thereby decreasing the amount of air aspirated with blood into the fluid collector 12 and, therefore, decreasing the turbulent flow in the fluid collector 12.

A value for a maximum threshold rate at which blood flows into the reservoir 18 may be programmed into the controller 54. The controller 54 may activate an alarm 56 if this threshold rate is exceeded, thereby notifying an operator of excessive patient bleeding. Conversely, a minimum threshold rate may be programmed into the controller 54. If the controller 54 does not detect at least this minimum rate of patient blood flow, the controller may also activate an alarm to notify an operator that the suction wand is not positioned correctly.

Further, the controller 54 may optionally instruct a peristaltic pump 70 associated with an anticoagulant line 72 to vary a rate at which the pump 70 is delivering an anticoagulant, from an anticoagulant reservoir 74, to the blood receiving reservoir 18, in response to the patient blood flow. It will be apparent to those skilled in the art that the anticoagulant may be added to received blood in the blood collector, 12, connective tubing line 14, as well as, in the reservoir 18. The controller 54 may vary the anticoagulant delivery rate with detected blood flow as described in U.S. Pat. No. 5,378,227(1995) to O'Riordan et al., the disclosure of which is herein incorporated by reference in its entirety.

Figure 5:
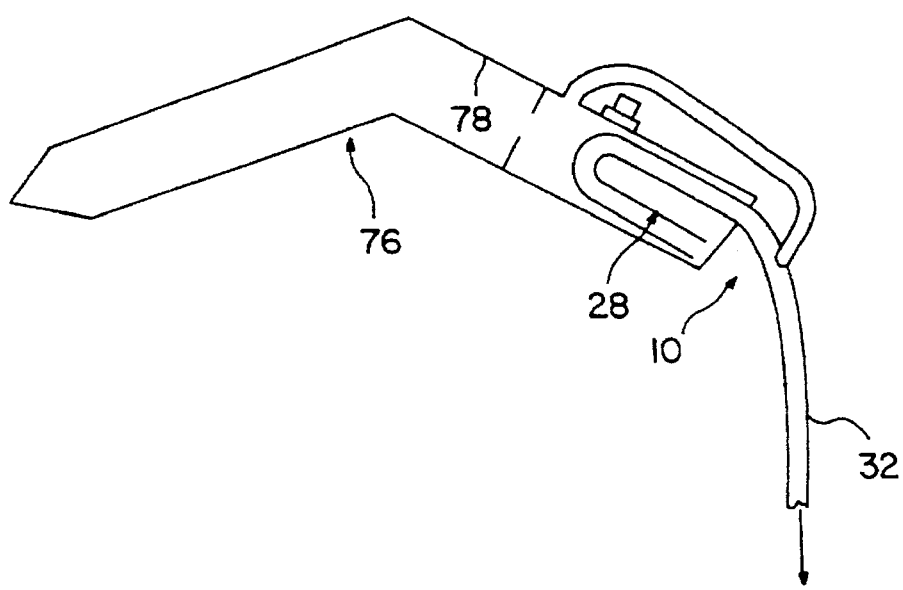
FIG. 5 is schematic diagram of a fluid receiver having the accumulator of the present invention disposed inside.

FIG. 5 illustrates a fluid receiver 76 having a blood accumulator 10 disposed in its interior. It will be apparent to those skilled in the art that the accumulator may be disposed in a fluid receiver 76 in any number of configurations. It is important, however, in this embodiment, that the first siphon length 28 be disposed at higher elevation than the external siphon length 32 in order for the siphon to function.

Although the present invention has been described with reference to preferred embodiments, numerous modifications and variations can be made and still the result will come within the scope of the invention. No limitation with respect to the specific embodiments disclosed herein is intended or should be inferred.

I claim:

1. An apparatus for accumulating surgical fluids, comprising:

a fluid collector;

a tubing connector attached to the fluid collector;

a reservoir in communication with the tubing connector, the reservoir having an interior and exterior;

a siphon, disposed in the reservoir interior, the siphon having a exterior siphon length extending beyond the reservoir exterior, the siphon length having a siphon end;

a vacuum source in communication with the siphon end; and a bypass line, the bypass line connecting a portion of the reservoir interior above the siphon to the exterior siphon length.

2. The apparatus of claim 1, further comprising a fluid level sensor in communication with the reservoir.

3. The apparatus of claim 2, further comprising a controller, the controller being in communication with the fluid level sensor and the vacuum source.

4. The apparatus of claim 3, further comprising an alarm, the alarm capable of being activated by the controller.

5. The apparatus of claim 4, wherein the fluid collector comprises a suction wand.

6. The apparatus of claim wherein 5, the vacuum source comprises a variable speed pump.

7. A method for collecting blood, comprising the steps of:

(a) receiving blood from a patient by applying a source of vacuum to a suction wand;

(b) transporting the received blood to a reservoir;

(c) removing air from the reservoir;

(d) accumulating the received blood to a predetermined volume in the reservoir;

(e) transporting the blood out of the reservoir in a bolus once the predetermined volume has been achieved;

(f) repeating steps (a) through (e) for a duration of a surgical procedure;

(g) sensing a fluid level when the received blood achieves the predetermined volume;

(h) measuring a time interval between each fluid level sensing;

(i) correlating each time a fluid level is sensed to the predetermined volume; and (j) determining a rate of total blood volume passing through the reservoir for a given time period.

8. The method of claim 7, further comprising the step of:

(k) adjusting the amount of vacuum applied to the suction wand in response to the determined blood flow rate.

9. The method of claim 8, further comprising the steps of:

(l) delivering anticoagulant to the received patient blood at a delivery rate; and (m) varying the delivery rate in response to the determined blood flow rate.

10. The method of claim 8, wherein the vacuum adjusting step (k) further comprises the substep of adjusting the amount of vacuum applied to the suction wand downward when the total blood volume rate decreases.

11. The method of claim 10, further comprising the step of:

(n) activating an alarm when the total blood volume rate exceeds a predetermined threshold rate.

12. A blood collection apparatus, comprising:

an accumulator comprising a fluid inlet, a fluid outlet, a gas outlet and a wall;

a siphon, having a first end, a second end and a top, disposed inside the accumulator, the second siphon end exiting the accumulator through the fluid outlet, thereby defining an external siphon length;

a bypass line, having a first and a second end, the first end connected to the gas outlet of the accumulator and the second end connected to the external siphon length; and a vacuum source connected to the second end of the siphon.

13. The apparatus of claim 12, further comprising a fluid level sensor communicating with the accumulator.

14. The apparatus of claim 13 further comprising means, communicating with the fluid level sensor, for counting each fluid level sensor activation.

15. The apparatus of claim 14, further comprising means, communicating with the fluid level sensor, for measuring a time interval between each fluid level sensor activation.

16. The apparatus of claim 15, further comprising means, communicating with the measuring means, for automatically increasing the vacuum in the accumulator when the total surgical fluid passing through the accumulator for a predetermined time period increases.

17. The apparatus of claim 16, further comprising an alarm in communication with the measuring means.

* * * * *